US010327718B2

(12) United States Patent
Kim et al.

(10) Patent No.: US 10,327,718 B2
(45) Date of Patent: Jun. 25, 2019

(54) DENTAL X-RAY IMAGING DEVICE

(71) Applicants: VATECH Co., Ltd., Gyeonggi-do (KR); VATECH EWOO Holdings Co., Ltd., Gyeonggi-do (KR)

(72) Inventors: Tae Woo Kim, Gyeonggi-do (KR); Byung Hun Park, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 0 days.

(21) Appl. No.: 16/174,251

(22) Filed: Oct. 29, 2018

(65) Prior Publication Data

US 2019/0059835 A1    Feb. 28, 2019

Related U.S. Application Data

(63) Continuation of application No. 15/107,469, filed as application No. PCT/KR2014/012755 on Dec. 23, 2014.

(30) Foreign Application Priority Data

Dec. 23, 2013    (KR) ........................ 10-2013-0161093

(51) Int. Cl.
*A61B 6/14*      (2006.01)
*A61B 6/00*      (2006.01)
*A61B 6/03*      (2006.01)

(52) U.S. Cl.
CPC ................. *A61B 6/14* (2013.01); *A61B 6/03* (2013.01); *A61B 6/42* (2013.01); *A61B 6/4233* (2013.01); *A61B 6/501* (2013.01)

(58) Field of Classification Search
CPC ........... A61B 6/15; A61B 6/03; A61B 6/4233; A61B 6/501
See application file for complete search history.

(56) References Cited

U.S. PATENT DOCUMENTS

| 4,709,382 | A | * | 11/1987 | Sones | ................... | A61B 6/032 |
| | | | | | | 378/146 |
| 5,214,686 | A | | 5/1993 | Webber | | |
| 5,930,330 | A | | 7/1999 | Wolfe et al. | | |
| 7,567,649 | B1 | * | 7/2009 | Safai | ........................ | G01T 1/24 |
| | | | | | | 250/370.09 |
| 2006/0067458 | A1 | | 3/2006 | Chen | | |
| 2006/0193429 | A1 | | 8/2006 | Chen | | |
| 2013/0010923 | A1 | | 1/2013 | Lee | | |

FOREIGN PATENT DOCUMENTS

| KR | 10-2007-0005036 A | 1/2007 |
| KR | 10-2011-0107032 A | 9/2011 |

\* cited by examiner

*Primary Examiner* — Courtney D Thomas
(74) *Attorney, Agent, or Firm* — IP Legal Services, LLC

(57) ABSTRACT

Disclosed is a dental X-ray imaging device having a curved detector. The dental X-ray imaging device according to the present invention comprises: an X-ray source for radially emitting X-rays; and a curved detector formed in a cylindrical two-dimensional curved shape or a round three-dimensional curved shape, which is arranged to be spaced apart at a predetermined distance from the X-ray source and has substantially the same radius of curvature as the predetermined distance.

10 Claims, 3 Drawing Sheets

DENTAL X-RAY IMAGING DEVICE

CROSS REFERENCE TO RELATED APPLICATIONS

This application is a Continuation of U.S. patent application Ser. No. 15/107,469 (filed on Jun. 23, 2016), which is a National Stage Patent Application of PCT International Patent Application No. PCT/KR2014/012755 (filed on Dec. 23, 2014) under 35 U.S.C. § 371, which claims priority to Korean Patent Application No. 10-2013-0161093 (filed on Dec. 23, 2013), the teachings of which are incorporated herein in their entireties by reference.

TECHNICAL FIELD

The present invention relates generally to a dental imaging device using X-rays and, more particularly, to a device for panoramic radiography, computed tomography, cephalometric radiography, or combination thereof, which are widely used in dental clinics.

BACKGROUND ART

In the medical field, an X-ray imaging device refers to a device that allows a predetermined amount of X-rays penetrates a body part to be radiographed, and provides an image by using electrical signals generated from an X-ray detector on which the penetrated X-rays are incident. The X-rays penetrated through the body part generate different electrical signals according to the X-ray attenuation ratio of a location of the body part, and thus an image is realized through the electrical signals and location information.

However, the energy of the X-rays incident on the X-ray detector is influenced not only by the attenuation ratio according to a penetration path but also by an incidence angle and a distance from the X-ray source to each location of the incidence surface of the X-ray detector. Accordingly, in order to obtain an accurate X-ray image, it is required the work of correction for X-ray energy differences due to the differences in distance and angle. Hereinbelow, reference will be made in greater detail to the difference with reference to the accompanying drawings.

FIG. 1a is a view illustrating that an X-ray image is obtained using a conventional flat detector. And FIG. 1b is a view illustrating differences in distance according to locations, on which X-rays are incident, in the conventional flat detector. In the conventional dental X-ray imaging device, generally, an X-ray source 10 is a cone-beam type that radially emits X-rays within a predetermined angle range, and an X-ray detector is a flat detector 20 that detects X-ray energy incident on a flat surface having a predetermined area. When X-rays are projected onto the flat detector 20, a distance to a center of the flat detector 20 is R1, and a distance to an edge of the flat detector is R2, thereby the X-rays traveling distances become different. Further, X-rays are incident on the center of the flat detector 20 at a right angle, and on the contrary, X-rays are incident on the edge of the flat detector at a tilted angle by a distance apart from the center. Due to the differences, the detected result is inaccurate, and thus to compensate for this, the work of correction for an incidence location on the flat detector is required.

DISCLOSURE

Technical Problem

Accordingly, the present invention has been proposed to solve the above problems, and the present invention is intended to propose a dental X-ray imaging device having a curved X-ray detector of which the parts are at an equal distance from the X-ray source.

Technical Solution

In order to achieve the above object, according to one aspect of the present invention, there is provided a dental X-ray imaging device including: an X-ray source radially emitting X-rays; and a curved detector spaced apart from the X-ray source at a predetermined distance, and formed in a cylindrical two-dimensional curved shape or in a spherical three-dimensional curved shape having a same radius of curvature as the predetermined distance.

The curved detector may include a plurality of pixels, wherein a curvature of each of the pixels, given that an incidence surface of each pixel has a tilted angle θ relative to an incidence surface of a neighboring pixel, satisfies a following expression of relation within an error range of 20%:

one pixel curvature=180°−2θ, wherein, θ=a cos ((a size of one pixel/2)/FDD) (wherein, FDD=the predetermined distance).

Advantageous Effects

According to the present invention having the above-described characteristics, it is possible to provide a dental X-ray imaging device having a curved X-ray detector of which the parts are at an equal distance from the X-ray source.

Thereby, it is possible to provide an accurate X-ray image without additional correction according to locations on the X-ray detector.

MODE FOR INVENTION

Reference will now be made in greater detail to exemplary embodiments of the present invention, an example of which is illustrated in the accompanying drawings. Although preferred embodiments of the present invention have been described for illustrative purposes, those skilled in the art will appreciate that various modifications, additions and substitutions are possible, without departing from the scope and spirit of the invention as disclosed in the accompanying claims.

Figure 1A:
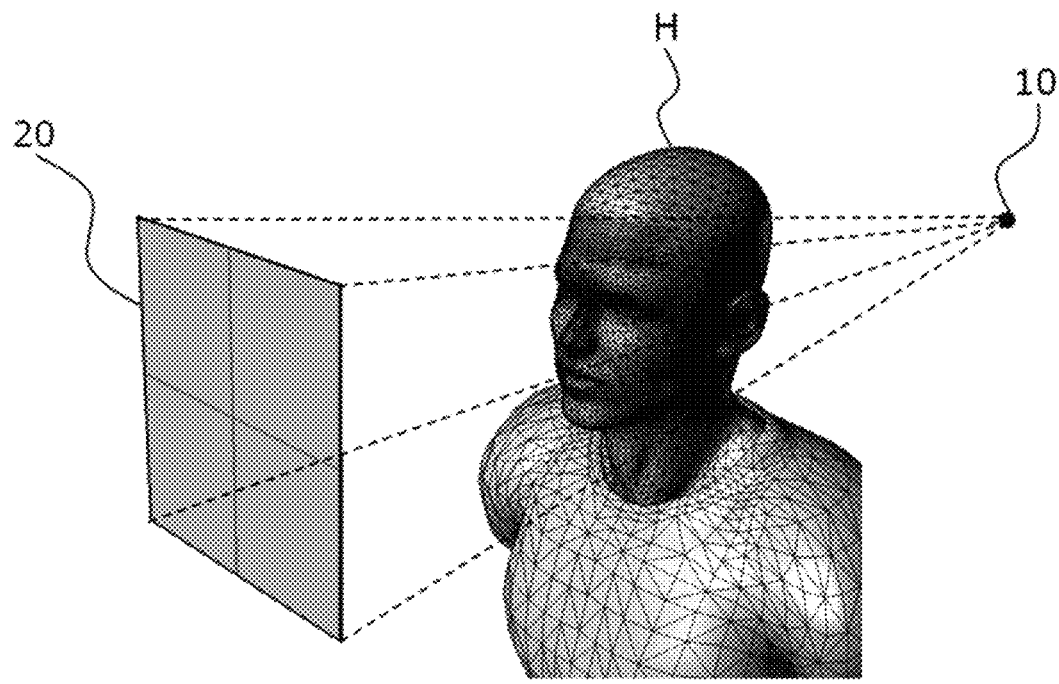
FIG. 1a is a view illustrating that an X-ray image is obtained by using a conventional flat detector.
Figure 1B:
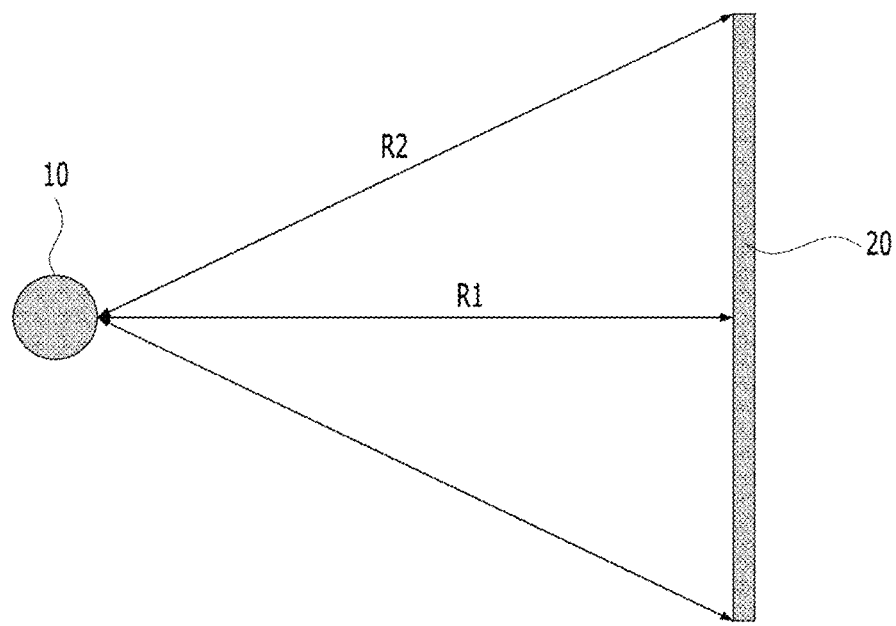
FIG. 1b is a view illustrating differences in distance according to locations, on which X-rays are incident, in the conventional flat detector.
Figure 2:
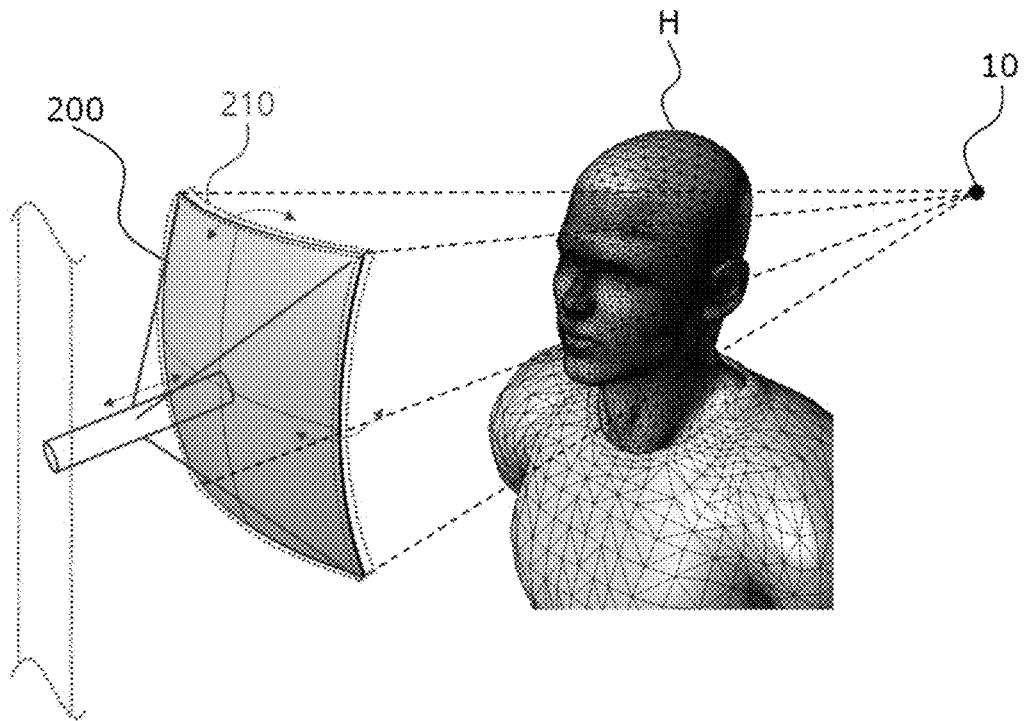
FIG. 2 is a view illustrating a curved detector according to an embodiment of the present invention.

FIG. 2 is a view illustrating a curved detector according to an embodiment of the present invention. The curved detector according to the present invention may be formed in a cylindrical two-dimensional curved shape or in a spherical three-dimensional curved shape. FIG. 2 schematically shows that an X-ray image of a head of a subject H is obtained by the three-dimensional curved (spherical) detector 200. X-rays emitted from an X-ray source 10 are incident on the three-dimensional curved detector 200 after penetrating the head of the subject H, wherein the entire incidence surface of the three-dimensional curved detector 200 has an equal X-ray path length and an equal incidence angle.

The curved detector 200 may be set to have a predetermined curvature when manufactured. However, if it is necessary, the curved detector 200 may be a flexible detector so as to be adjusted and set to have the predetermined curvature by a support frame, such as a jig.

Further, the curved detector 200 may include a plurality of pixels. At least a part of the plurality of pixels may be configured to have a triangular shape to make it advantageous to design a two-dimensional curved (cylindrical) shape or a three-dimensional curved (spherical) shape.

Figure 3:
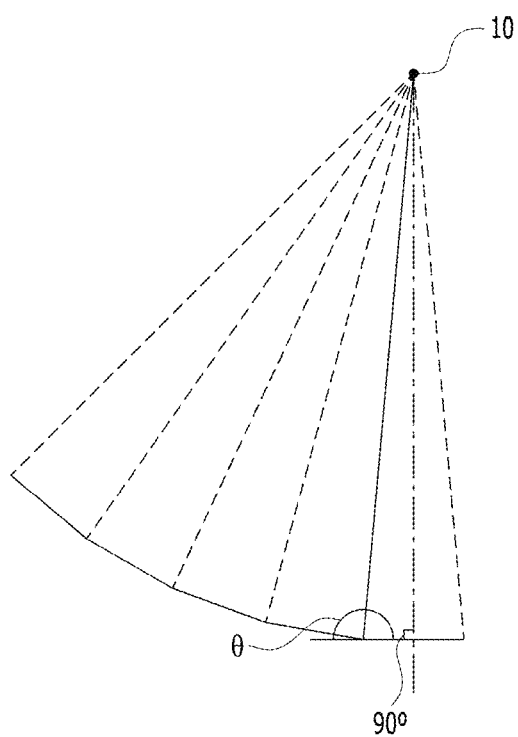
FIG. 3 is an enlarged view of the curved detector according to the embodiment of FIG. 2.

FIG. 3 is an enlarged view of the curved detector according to the embodiment of FIG. 2. In a sectorial shape shown in FIG. 3, the X-ray source 10 is disposed at a location defining a vertex, and an arc of the sectorial shape refers to a part of the curved detector 200 including the plurality of pixels.

In order for the entire incidence surface of each pixel to have an equal distance from the X-ray source to an incidence surface (focus-to-detector distance, FDD), a curvature of each pixel and a curvature of the curved detector are determined by the following expression of relationship.

Given that an incidence surface of each pixel has a tilted angle θ relative to an incidence surface of a neighboring pixel, θ=a cos((a size of one pixel/2)/FDD), one pixel curvature=180°−2θ, a curvature of the curved detector=one pixel curvature×a length of the detector/2

Of the curved detector 200 according to the embodiment, the curvature of each pixel and the curvature of the curved detector may be obtained from the above relationship. Further, if the detector is applied to a dental X-ray imaging device, the detector can be set to have a curvature value obtained from the above relationship within an error range of ±20%, thereby obtaining the aimed effect through the present invention.

To be more specific, in the dental X-ray imaging device, for example, when the above relationship is applied to a case where a size of a pixel is 200 μm×200 μm, a size of the curved detector is 145 mm×116 mm, and the FDD is 640 mm, the following values are obtained:

one pixel curvature=0.02°, a horizontal curvature of the curved detector=6.49°, a vertical curvature of the curved detector=5.19°.

The curvature of the curved detector may be obtained from a size of a pixel, a size of the detector, and a value of the FDD by using the above relationship. In the dental X-ray imaging device, the curved detector may be applied to a detector for panoramic radiography, a detector for computed tomography, or a detector for cephalometric radiography. If each pixel has an equal size, the curvature of the curved detector may vary depending on the value of the FDD.

Figure 4:
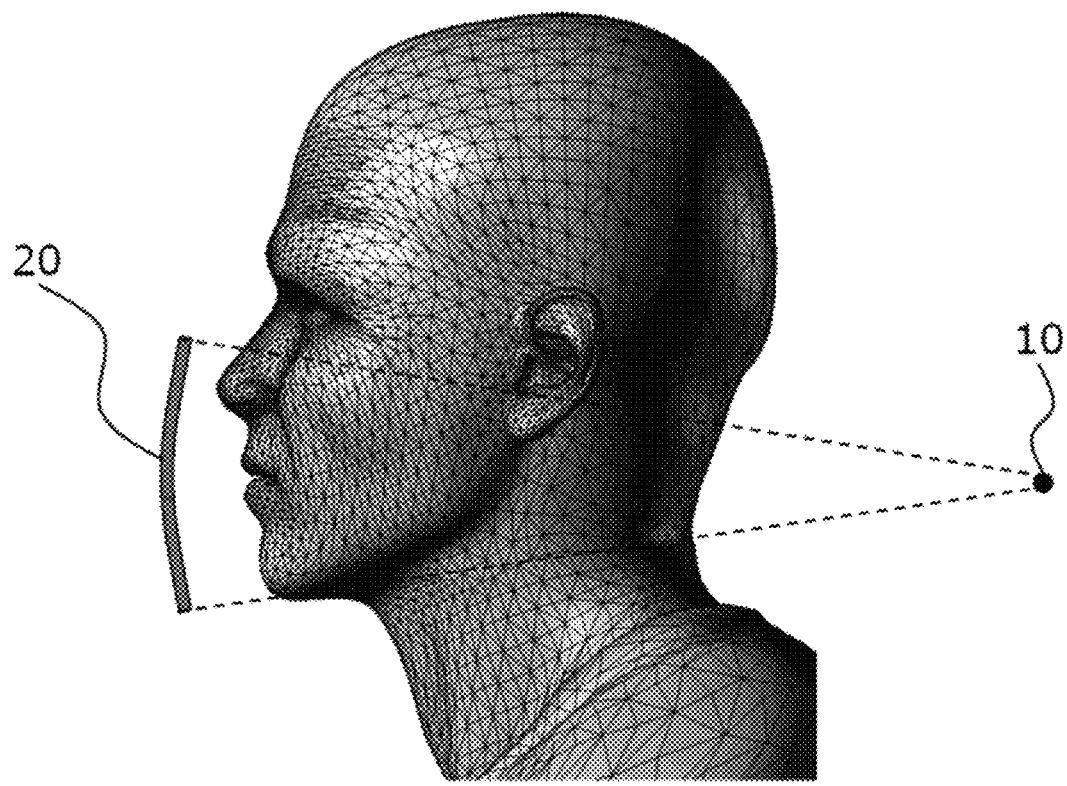
FIG. 4 is a view illustrating a curved detector according to another embodiment of the present invention.

FIG. 4 is a view illustrating a curved detector according to another embodiment of the present invention. FIG. 4 illustrates that the curved detector 200 according to the present invention is applied as a detector for panoramic radiography of the dental X-ray imaging device. The curved detector 200 may be formed in a two-dimensional curved shape having a curvature only in a vertical direction, or may be formed in a three-dimensional curved (spherical) shape having curvatures in both a vertical direction and a depth direction in the drawing. In either case, the detector for panoramic radiography may be formed in a shape that a length of the depth direction is shorter than a length of the vertical direction in the drawing. The curvature of the curved detector 200, the size of a pixel forming the detector, and the distance from the X-ray source 10 (FDD) may satisfy the relationship described referring to the embodiment of FIG. 3, or may satisfy the relationship within an error range of ±20%.

The invention claimed is:

1. A dental X-ray imaging device comprising:
an X-ray source configured to emit X-rays;
an X-ray detector having a flexible incidence surface; and
a support frame configured to adjust a curvature of the X-ray detector,
wherein the support frame is configured to vary the coverture of the X-ray detector depending on the distance from the X-ray source to an incident surface.

2. The dental X-ray imaging device of claim 1, wherein the dental X-ray imaging device is configured for panoramic radiography, computed tomography, cephalometric radiography, or combination thereof.

3. The dental X-ray imaging device of claim 1, wherein the support frame is configured to adjust the curvature of the X-ray detector to have a three-dimensional curved shaped with curvatures in a vertical direction and a horizontal direction.

4. The dental X-ray imaging device of claim 3, wherein a horizontal curvature is larger than a vertical curvature.

5. The dental X-ray imaging device of claim 1, wherein the X-ray detector includes a plurality of pixels being in contact with each other at a predetermined angle along the incidence surface.

6. The dental X-ray imaging device of claim 1, wherein the X-ray detector includes a plurality of pixels having an equal size.

7. The dental X-ray imaging device of claim 1, wherein the detector includes a plurality of pixels, wherein a curvature of each of the pixels, given that an incidence surface of each pixel has a tilted angle θ relative to an incidence surface of a neighboring pixel, satisfies a following expression of relation within an error range of 20%:

one pixel curvature=180°−2θ, wherein, θ=a cos (a size of one pixel/2)/FDD (wherein, FDD=the predetermined distance).

8. A dental X-ray imaging device for panoramic radiography comprising:
an X-ray source configured to emit X-rays to produce a panoramic image;
an X-ray detector having a flexible incidence surface, wherein the detector includes a plurality of pixels, wherein a curvature of each of the pixels, given that an incidence surface of each pixel has a tilted angle θ relative to an incidence surface of a neighboring pixel, satisfies a following expression of relation within an error range of 20%:

one pixel curvature=180°−2θ, wherein, θ=a cos (a size of one pixel/2)/FDD (wherein, FDD=the predetermined distance); and
a support frame configured to adjust a curvature of the X-ray detector,
wherein the support frame is configured to adjust the curvature of the X-ray detector to have at least one of (1) a three-dimensional curved shaped with curvatures in a vertical direction and a horizontal direction and (2)

a two-dimensional curved shape having a curvature only in a vertical direction.

9. The dental X-ray imaging device of claim 8, wherein the X-ray detector includes a plurality of pixels being in contact with each other at a predetermined angle along the incidence surface.

10. The dental X-ray imaging device of claim 8, wherein the X-ray detector includes a plurality of pixels having an equal size.

\* \* \* \* \*